United States Patent [19]

Lautenschläger et al.

[11] 4,287,894
[45] Sep. 8, 1981

[54] APPARATUS FOR PRODUCING A SERIES OF IMPULSES CORRESPONDING TO A SUCCESSION OF PULSE BEATS

[75] Inventors: Peter Lautenschläger, Gonbach; Michael Teichmann, Obermoschel, both of Fed. Rep. of Germany

[73] Assignee: Keiper Dynavit GmbH & Co., Fed. Rep. of Germany

[21] Appl. No.: 46,719

[22] Filed: Jun. 8, 1979

[30] Foreign Application Priority Data

Jun. 9, 1978 [DE] Fed. Rep. of Germany ....... 2825327

[51] Int. Cl.³ .............................................. A61B 5/02
[52] U.S. Cl. .................................... 128/687; 307/358
[58] Field of Search ....................... 307/262, 311, 358; 328/155; 329/122–124; 128/687–690, 702–708

[56] References Cited

U.S. PATENT DOCUMENTS

| | | | |
|---|---|---|---|
| 3,746,997 | 7/1973 | Willett et al. | 329/122 |
| 3,768,030 | 10/1973 | Brown et al. | 329/122 |
| 3,986,498 | 10/1976 | Lewis | 128/706 |
| 4,055,814 | 10/1977 | Abraham et al. | 328/155 |
| 4,065,668 | 12/1977 | Monticelli | 307/311 |
| 4,149,526 | 4/1979 | Bargenda et al. | 128/706 |
| 4,182,315 | 1/1980 | Vos et al. | 128/687 |

*Primary Examiner*—Robert W. Michell
*Assistant Examiner*—Francis J. Jaworski
*Attorney, Agent, or Firm*—Wigman & Cohen

[57] ABSTRACT

The present invention relates to an apparatus for producing a succession of pulses corresponding to the succession of pulse beats of a person. The apparatus has a pulse detector and at least one stage subsequent to the pulse detector to suppress disruptive influences. The invention is characterized by a voltage-controlled pulse generator which is controlled by a comparator. The comparator compares the contents of two memories of which the first stores the pulse coming from the pulse detector and the second stores the pulse appearing at the output of the pulse generator.

8 Claims, 1 Drawing Figure

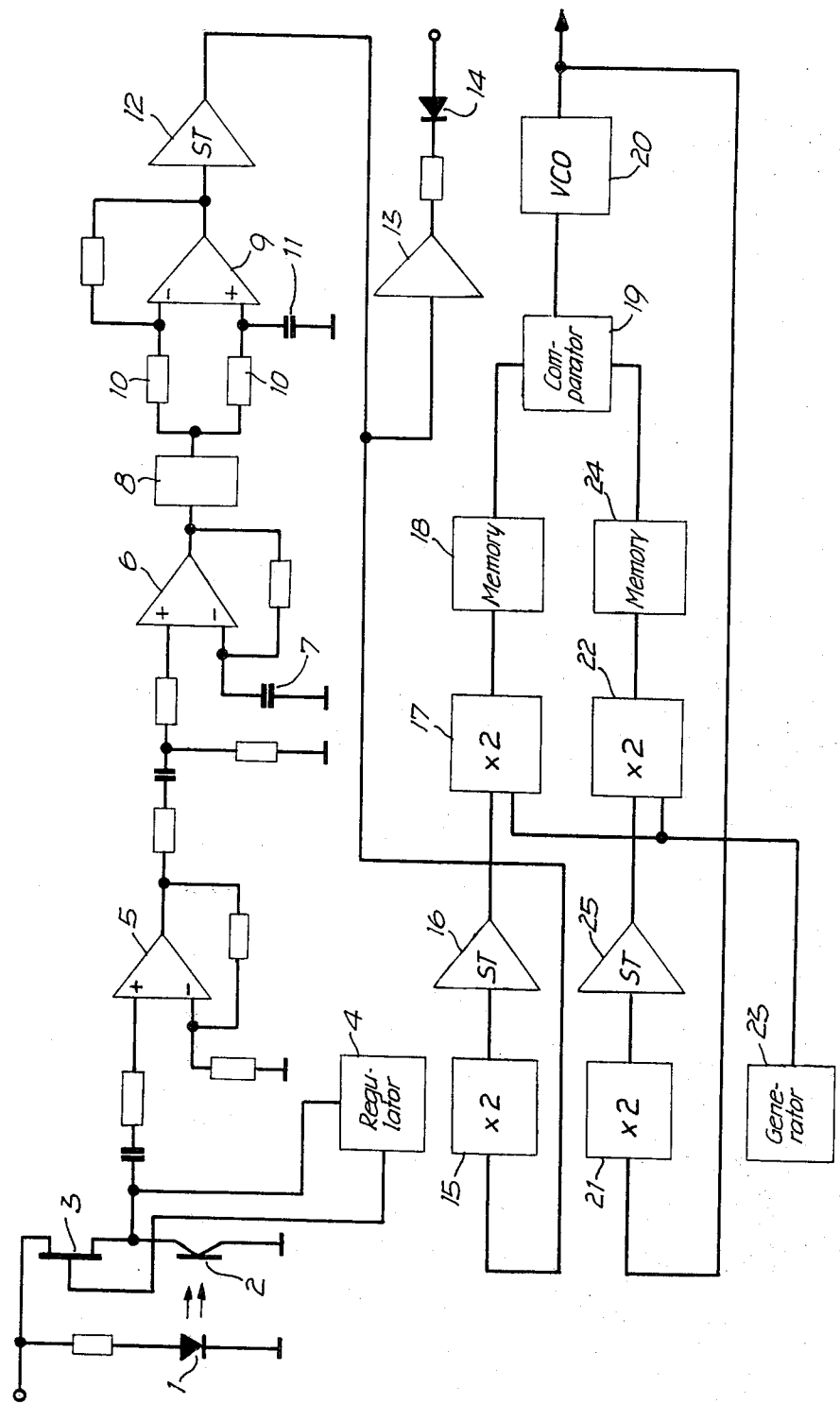

APPARATUS FOR PRODUCING A SERIES OF IMPULSES CORRESPONDING TO A SUCCESSION OF PULSE BEATS

BACKGROUND OF THE INVENTION

1. Field of the Invention

The invention relates to an apparatus for producing a series of pulses corresponding to a series of pulse beats of a person. The invention has a pulse detector and at least one stage for suppressing disturbing influences connected behind the pulse detector.

2. Description of the Prior Art

It is known to suppress influences in the form of disturbing signals with the aid of filters. It is also known to separate the signals coming from the pulse detector from disturbing signals with the aid of amplifiers whose amplification can be controlled. Disturbing influences can, however, also lead to the signals corresponding to pulse beats being completely or partially suppressed. Particularly in taking a pulse on the earlobes of a person, muscle flexings can lead to the pulse taker transmitting no pulses which correspond to pulse beats.

SUMMARY OF THE INVENTION

The basic objective of the invention is to create an apparatus which produces a series of pulses corresponding to a series of pulse beats of a person. The present invention is better able to suppress disturbing influences than in known devices of this type. This objective is achieved according to the invention by a voltage-controlled pulse generator which is controlled by a comparator. This comparator compares the content of two memories, of which the first stores pulses coming from the pulse detector and of which the second temporarily stores the pulses appearing at the output of the pulse generator.

The voltage-controlled pulse generator thereby lies in a regulating circuit, for which reason the frequency of its output pulse is continually regulated with regard to the frequency of the pulse coming from the pulse detector. If one or more of these pulses is missed, then in this time period the value stored in the memory is available to form the adjusting value, by which means this disruption is prevented from having an effect on the pulse frequency at the output of the voltage-controlled generator.

If brief disruptions must be compensated for, whose frequency corresponds to a pulse frequency lying above a limiting value, then by limiting the memory capacity of the two memories the pulse frequency at the output of the voltage-controlled cycle generator can be prevented from increasing accordingly.

In order to be able to level out any potential deviation of the output frequency of the pulse generator as quickly as possible when a pulse corresponding to a pulse beat appears, at least one multiplying stage, which multiplies the succession of pulses fed to it by the same factor, is connected in front of each of the two memories, and these multiplying stages are synchronized. For this purpose, the two multiplying stages can be controlled by a generator which produces a synchronizing pulse.

In a preferred exemplary embodiment, an operational amplifier is connected behind the pulse detector, whose non-inverting input is connected to ground by means of a capacitor, and whose two inputs, which are connected in front of resistors of the same value, are driven simultaneously by the same signals coming from the pulse detector. By means of this amplifier circuitry, a floating trigger threshold is achieved, whereby the signals beneath the threshold do not arrive at the amplifier output and all signals above this threshold are amplified to a maximum value.

Disturbances, such as can appear, for example, during substantial body movements, can lead to a very high d.c. voltage content of the pulses. In order to suppress these disturbing influences, an operational amplifier can be connected behind the pulse detector, whose non-inverting input is controlled by the signals coming from the pulse detector and whose inverting input is connected to ground by means of a capacitor.

In this manner, an amplification of the equal voltage proportion is avoided. Preferably, this operational amplifier is arranged between the pulse detector and the operational amplifier which forms the floating trigger threshold.

In taking a pulse from an earlobe or a finger, the conductivity or reflection capacity, which varies from person to person, can be very different for the signals emanating from the sender. In a preferred exemplary embodiment, the pulse detector, therefore, has a light-sensitive receiver, which has an operating point controlled by a regulator. In this manner, the level of the output pulses of the detector is independent of the varying pulse-taking conditions.

In a particularly simple manner, the stabilization of the operating point is possible with the aid of a regulator, which controls the operating point of the receiver formed by a phototransmitter by means of a field-effect transistor connected in series with the photo-transistor in dependence on the level of the output signals of the receiver.

BRIEF DESCRIPTION OF THE DRAWING

The invention is described in greater detail below with the aid of an exemplary embodiment illustrated in the drawing. The single FIGURE shows a block circuit diagram of the exemplary embodiment.

DESCRIPTION OF THE PREFERRED EMBODIMENT

An apparatus for producing a series of pulses corresponding to a series of pulse beats of a person has a pulse detector which can be attached to the earlobe or the finger of a person. The apparatus consists of a sender 1 and a receiver 2 which in the exemplary embodiment operate optoelectronically. The sender 1 is formed by a light-emitting diode which directs a light beam of constant intensity to the blood vessels in the earlobe or in the finger. Of course, if one must deal with disturbance light or must save energy, a pulse mechanism can be provided for the sender 1. The intensity of the light beam is modulated in dependence on the pulse beat through the blood vessels, through which it passes or on which it is reflected. On the other hand, its intensity will be decreased to a degree that will vary with each individual person, for example, because of different thicknesses of earlobes or fingers. In order to compensate for these personal differences and thereby obtain signals of approximately the same level at the output of the receiver for all persons, a field-effect transistor 3 is connected in series with the collector-emitter line of the receiver 2 operating as a photo-transistor. The field-effect transistor 3 has a control electrode connected to a regulator 4 to which the output signal of the receiver 2 is transmitted. The regulator 4 adjusts the photo-transistor to the same operating point independent of the thickness of the earlobe or finger. The regulator 4 consists of at least one operation amplifier (for instance LM 324 of Texas Instruments or 741 of National Semiconductors, both U.S.A.). The regulator 4 and the transistor 3, which could also be a bipolar transistor, form a loop. The loop amplifier of this loop is negative and includes the filter process of a band elimination in the frequency range of the heartbeat of about 0.8 to 4 Hz. Outside of this frequency range, the loop amplification which is, for example, −10 causes:

(1) a stabilization of the operating point of the phototransistor 2, which is preferably set at one-half of the supply voltage of the series circuit of transistor 3 and phototransistor 2 by a reference voltage in the regulator 4 to achieve maximum sensitivity; and (2) a suppression of disturbing signals above the frequency range. The loop amplification increases overproportionally and nonlinearly for signal amplitudes greater than the heartbeat signals to be expected.

The output signals of the receiver 2 are amplified by means of a first amplifier 5, which in the exemplary embodiment is an operational amplifier, whose inverting input, to which the output is fed back, is connected to ground by means of a resistor. The first amplifier 5 is formed as a band pass filter.

After the first amplifier 5, there follows a second amplifying stage 6, whose operational amplifier has a capacitor 7 instead of a grounding resistor. The capacitor, which on one end is connected to ground, is connected to the inverting input on the other end, which in turn is connected by a resistor at the output of the operational amplifier.

The output signals of the second amplifying stage 6 are transmitted to a third amplifying stage 9 via a band pass filter 8. The amplification of the signals takes place at this stage also with the aid of an operational amplifier. In contrast to the operational amplifiers of the previous stages, however, here a resistor 10 is connected in front of each of the two inputs. These two resistors 10, which have the same value, are connected on the other end with the output of the band pass filter 8, so that its output signals simultaneously drive the two inputs of the operational amplifier. The non-inverting input of the operational amplifier of amplifying stage 9 is connected via a capacitor 11 to ground, and the inverting input is connected with the output of the operational amplifier via a resistor. By means of this circuitry of the operational amplifier, the amplifier obtains a floating, i.e., signal-dependent varying trigger threshold, by means of which signals below a predetermined voltage value cannot arrive at the output of the amplifying stage 9 and signals above this voltage value are amplified to a maximum value. The third amplifying stage 9 thus acts similarly to a Schmitt trigger, but distinguishes itself from such a trigger by its floating trigger threshold. In the exemplary embodiment, only signals above 1.2 volts peak-to-peak are amplified. Signals lying below this level are suppressed. An advantage of the third amplifying stage 9 consists further therein that the input signals can have a positive or a negative equal voltage proportion up to the level of the supply voltage without this stage losing its special amplifying characteristics. The sensitivity of the third amplifying stage 9 is dependent on the size of the capacitor 11.

The third amplifying stage 9 is connected behind a Schmitt trigger 12, whose output pulses control an amplifier 13, which in turn drives a light-emitting diode 14. Because each output pulse is produced by the r points of the pulse signals corresponding to the pulse beats, the light-emitting diode 14 is illuminated in rhythm with the appearance of the r points, which correspond to the beat rhythm of the heart.

The term "r point" is used in connection with the R point of the QRS wave complex of an electrocardiogram; however, it should not be confused therewith. However, each peripheral pressure wave has a spike, like the R spike of the QRS wave complex. Therefore, the pulse signals also have a spike. This spike is referred to herein as the "r point."

The output pulses of the Schmitt trigger 12 are not transmitted only to the amplifier 13, but also to a first multiplying circuit 15, which is connected behind a second multiplying circuit 17 with an intermediate Schmitt trigger 16. The pulse multiplication achieved with the aid of these two multiplying circuits 15 and 17 could, of course, also be achieved with a single circuit. In the exemplary embodiment, the two multiplying circuits each double the number of input pulses. By means of the pulse multiplication, a uniform voltage is achieved even in lower frequency regions.

The first memory 18 is connected behind the second multiplying circuit 17, which is capable of storing the pulses for about 3 seconds. The memory capacity is time-limited, however, so that brief disturbances, which result in pulse frequencies above a predetermined limit of, for example, 260 pulse beats per minute, can be suppressed because of insufficient memory capacity storage time.

The output of the first memory 18 is connected with one input of a comparator 19, which controls a voltage-controlled pulse generator 20, also known as a VCO, which is connected therebehind. The frequency of the pulses produced by the cycle generator 20 is dependent on the signal coming from the comparator 19. On the basis of the pulses produced by the cycle generator 20, the number of pulse beats permitted can be determined and, for example, indicated on a display. If an average value determination is desired or necessary, the output pulses of the pulse generator 20 can be, for example, transmitted to a computer, which undertakes the average value determination.

The pulses appearing at the output of the cycle generator 20, as the circuit diagram indicates, are also transmitted to a third multiplying circuit 21, which, like the first multiplying circuit 15, doubles the number of the pulses. By means of a subsequent Schmitt trigger 25, these pulses are transmitted to a fourth multiplying circuit 22, which again doubles the number of pulses. Like the multiplying circuits 15 and 17, the multiplying circuits 21 and 22 could also be replaced by a single multiplying circuit. A synchronizing generator 23 synchronizes the second multiplying circuit 17 with the fourth multiplying circuit 22. Generator 23 is a Schmitt trigger, the output of which is connected with its input by a capacitor and the input of which is connected to ground by a resistor. This causes the Schmitt trigger to oscillate. The frequency of the output depends upon the values of the capacitor and resistor as is well known. In the present embodiment, the frequency is, for example, 180 Hz. The generator 23 may be a ST 4093 CMOS, as manufactured by most CMOS manufacturers. This type of synchronization is necessary because the two series of pulses, which are produced with the aid of the multiplying circuits, must be synchronized, i.e., must have pulses of equal height and width. Only then is the comparator 19 in a position to compare the two frequencies. In the exemplary embodiment, the storage of the pulses appearing at the output of the second multiplying circuit 17 takes place in the form of an integration in the first memory 18. Accordingly, a second memory 24 which is connected behind the fourth multiplying circuit 22 integrates the pulses produced thereby. The second memory 24 is connected with the second input of the comparator 19, so that this comparator 19 can compare the memory contents and, thus, the frequency of the series of pulses coming from the pulse detector with the frequency of the series of pulses appearing at the output of the pulse generator 20. If the comparator 19 detects a deviation, then this deviation is leveled out by a change in the frequency of the pulse generator 20, namely, because of the multiplication of the pulses coming from the pulse detector within a very brief time. Because of the return of the output value of the pulse generator 20, a closed regulating circuit is achieved, in which deviations of the pulse frequency at the output of the pulse generator 20 from the pulse frequency at the output of the first memory 18, which is proportional to the heartbeat frequency, are leveled out very quickly. With so-called missing pulses, i.e., when pulses of the receiver 2 are missing, as can occur because of muscle flexings primarily while taking a pulse at the earlobes, the pulse frequency of the pulse generator 20 is, however, not regulated downward, in case the time period in which the receiver produces no pulses is not larger than three seconds. The memories 18 and 24 can store the last valid values for approximately three seconds, and these stored values are transmitted to comparator 19 until new values are present or the maximum memory time has been exceeded. Brief disturbances in the form of missing pulses are, therefore, completely suppressed.

Memories 18 and 24 are analog memories for storing direct voltages. They are constructed of capacitors in a known manner. The second multiplying circuit 17 is connected behind a first memory 18, which is preferably a RC integrator and forms the average voltage value from the incoming voltage pulses. The memory 18 can store the average value proportional to the number of pulses per unit of time with a time constant of several seconds.

The precision of the comparator 19 and the quality of the regulation of the regulating circuit are selected in the exemplary embodiment so that deviations of one pulse per minute are still leveled out. The regulating range extends from thirty pulse beats per minute to 260 pulse beats per minute.

Thus, disturbing influences are suppressed in different manners, depending upon their type. Brief disruptive influences whose frequencies lie above the limit value of the pulse frequency are suppressed by a limit of the memory capacity of the two memories 18 and 24. Disturbing influences due to pulses obtaining a direct current voltage content (i.e., disturbances such as those that can be caused by movements of the body) are suppressed by the amplifier 6 and the elements connected thereto, particularly the capacitor 7. Disturbing influences which result in signals below a certain peak voltage value (for example, 1.2 volts peak-to-peak in the exemplary embodiment) are suppressed by means of the amplifier 9. A false display of the heartbeat frequency is then prevented if temporarily no pulse is produced on the ear pulse receiver, such as can be the case with muscle flexing, by means of the VCO 20 in conjunction with the memories 18 and 24 and the comparator 19.

As a result of the various measures for suppressing disturbing influences, the pulse frequency which can be taken from the pulse generator 20 is practically free from disturbances.

The average value determination of the output pulse of the VCO 20 can be made by a known microprocessor, for instance, a Motorola 6801, Intel 8021, or Texas Instruments TMS 1000. The microcomputer determines the average period of, for instance, 16 pulses of the VCO 20 by dividing the time needed for receiving these pulses by the number of pulses.

Although only a preferred embodiment is specifically illustrated and described herein, it will be appreciated that many modifications and variations of the present invention are possible in light of the above teachings and within the purview of the appended claims without departing from the spirit and intended scope of the invention.

We claim:

1. An apparatus for producing a succession of pulses corresponding to the succession of pulse beats of a person, said apparatus having a pulse detector and at least one stage means, arranged subsequent to said pulse detector, for suppressing disruptive influences, comprising:

a voltage-controlled pulse generator, first and second memory means, a comparator means for controlling said pulse generator and for comparing contents of said first and second memories, whereby disturbances in the form of missing pulses may be suppressed, said first memory being coupled to the output of said pulse detector and having means for storing a pulse coming from the pulse detector, and said second memory being coupled to the output of said pulse generator and having means for storing a pulse appearing at an output of the pulse generator.

2. Apparatus according to claim 1, wherein each of the first and second memories are connected behind at least one multiplying stage means for multiplying a succession of pulses fed thereto.

3. An apparatus for producing a succession of pulses corresponding to the succession of pulse beats of a person, said apparatus having a pulse detector and at least one stage means, arranged subsequent to said pulse detector, for suppressing disruptive influences, comprising:

a voltage-controlled pulse generator, a comparator means for controlling said pulse generator and for comparing contents of first and second memories, said first memory having means for storing a pulse coming from the pulse detector, said second memory having means for storing a pulse appearing at an output of the pulse generator, each of said first and second memories being connected behind at least one multiplying stage means for multiplying a succession of pulses fed thereto, and said multiplying stage means are controlled by a generator means for producing a synchronizing pulse.

4. Apparatus according to claim 1, wherein the memory capacities of the first and second memories are limited to a value corresponding to an upper limit of a heartbeat frequency.

5. An apparatus for producing a succession of pulses corresponding to the succession of pulse beats of a person, said apparatus having a pulse detector and at least one stage means, arranged subsequent to said pulse detector, for suppressing disruptive influences, comprising:

a voltage-controlled pulse generator, a comparator means for controlling said pulse generator and for comparing contents of first and second memories, said first memory having means for storing a pulse coming from the pulse detector, said second memory having means for storing a pulse appearing at an output of the pulse generator, and an operational amplifier connected behind the pulse detector whose non-inverting input is grounded via a capacitor and whose two inputs, which are connected in front of resistors of the same value, are driven simultaneously with the same signals coming from the pulse detector.

6. An apparatus for producing a succession of pulses corresponding to the succession of pulse beats of a person, said apparatus having a pulse detector and at least one stage means, arranged subsequent to said pulse detector, for suppressing disruptive influences, comprising:

a voltage-controlled pulse generator, a comparator means for controlling said pulse generator and for comparing contents of first and second memories, said first memory having means for storing a pulse coming from the pulse detector, said second memory having means for storing a pulse appearing at an output of the pulse generator, and an operational amplifier connected behind the pulse detector whose non-inverting input is driven by signals coming from the pulse detector and whose inverting input, connected with an output, is connected to ground via a capacitor.

7. An apparatus for producing a succession of pulses corresponding to the succession of pulse beats of a person, said apparatus having a pulse detector and at least one stage means, arranged subsequent to said pulse detector, for suppressing disruptive influences, comprising:

a voltage-controlled pulse generator, a comparator means for controlling said pulse generator and for comparing contents of first and second memories, said first memory having means for storing a pulse coming from the pulse detector, said second memory having means for storing a pulse appearing at an output of the pulse generator, and said pulse detector includes a light-sensitive receiver with an operating point controlled by a regulator.

8. Apparatus according to claim 7, wherein that the regulator controls the operating point of the receiver formed by a photo-transistor and a field-effect transistor connected in series with the photo-transistor in dependence on the level of the output signals of the receiver.

* * * * *